US012774751B2

(12) United States Patent
Mujwid et al.

(10) Patent No.: US 12,774,751 B2
(45) Date of Patent: *Oct. 27, 2026

(54) BI-DIRECTIONAL VALVE PUMP

(71) Applicant: Boston Scientific Scimed, Inc., Maple Grove, MN (US)

(72) Inventors: James Ryan Mujwid, Hudson, WI (US); Ryan Earl Fredrick, Eden Prairie, MN (US); Mark Edward DiLoreto, Chaska, MN (US); John Anders Bostrom, Minneapolis, MN (US); Jessica Elizabeth Felton, Minneapolis, MN (US); Thomas Andrew Albrecht, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 978 days.

This patent is subject to a terminal disclaimer.

(21) Appl. No.: 18/064,634

(22) Filed: Dec. 12, 2022

(65) Prior Publication Data

US 2023/0116352 A1 Apr. 13, 2023

Related U.S. Application Data

(63) Continuation of application No. 16/680,141, filed on Nov. 11, 2019, now Pat. No. 11,549,598.

(Continued)

(51) Int. Cl.
*F16K 11/02* (2006.01)
*A61F 2/26* (2006.01)
(Continued)

(52) U.S. Cl.
CPC .............. *F16K 11/027* (2013.01); *A61F 2/26* (2013.01); *F16K 15/04* (2013.01); *F16K 15/202* (2013.01)

(58) Field of Classification Search
CPC ...... F16K 11/027; F16K 15/04; F16K 15/202; F16K 15/18; F16K 15/1823;
(Continued)

(56) References Cited

U.S. PATENT DOCUMENTS

| | | | | |
|---|---|---|---|---|
| 4,782,826 A * | 11/1988 | Fogarty | A61F 2/26 600/40 |
| 5,010,882 A * | 4/1991 | Polyak | A61F 2/26 600/40 |

(Continued)

FOREIGN PATENT DOCUMENTS

| | | |
|---|---|---|
| CN | 108778191 A | 11/2018 |
| WO | 2011057642 A1 | 5/2011 |

(Continued)

OTHER PUBLICATIONS

Notice of Allowance for Chinese Application No. 201980074006.4 (with English translation), mailed Jun. 24, 2024, 6 pages.

(Continued)

*Primary Examiner* — Sunita Reddy
(74) *Attorney, Agent, or Firm* — Brake Hughes Bellermann LLP

(57) ABSTRACT

According to an aspect, an inflatable penile prosthesis includes a fluid reservoir configured to hold fluid, an inflatable member, and a pump assembly configured to transfer the fluid between the fluid reservoir and the inflatable member. The pump assembly includes a valve body, a pump bulb, and a deflation mode actuator. The valve body includes a bi-directional valve configured to move from an inflation position to a deflation position in response to an activation of the deflation mode actuator. The bi-directional valve in the inflation position is configured to open a fluid passageway in the valve body to transfer fluid from the pump bulb to the inflatable member. The bi-directional valve in the deflation position is configured to open a fluid passageway (Continued)

in the valve body to transfer fluid from the inflatable member to the fluid reservoir that bypasses the pump bulb.

18 Claims, 15 Drawing Sheets

Related U.S. Application Data

(60) Provisional application No. 62/768,406, filed on Nov. 16, 2018.

(51) Int. Cl.
*F16K 15/04* (2006.01)
*F16K 15/20* (2006.01)

(58) Field of Classification Search
CPC .... F16K 15/205; A61F 2/26; A61F 2250/006; A61F 2250/008
USPC ...................................................... 600/38–41
See application file for complete search history.

(56) References Cited

U.S. PATENT DOCUMENTS

| | | | | |
|---|---|---|---|---|
| 6,171,233 | B1 * | 1/2001 | Willard | A61F 2/26 600/40 |
| 8,257,246 | B1 * | 9/2012 | Fogarty | A61F 2/26 600/40 |
| 8,337,392 | B2 * | 12/2012 | Morningstar | A61F 2/26 600/40 |
| 9,554,937 | B2 | 1/2017 | Daniel | |
| 2002/0082472 | A1 | 6/2002 | Derus et al. | |
| 2003/0100929 | A1 * | 5/2003 | Forsell | A61F 2/26 607/39 |
| 2003/0114729 | A1 * | 6/2003 | Forsell | A61F 2/26 600/38 |
| 2007/0142700 | A1 | 6/2007 | Fogarty et al. | |
| 2008/0114202 | A1 * | 5/2008 | Kuyava | A61F 2/26 600/38 |
| 2011/0201880 | A1 | 8/2011 | Fogarty | |
| 2013/0072751 | A1 | 3/2013 | Fogarty | |
| 2015/0359655 | A1 * | 12/2015 | Daniel | A61F 5/41 600/40 |
| 2018/0042724 | A1 | 2/2018 | Diloreto | |
| 2018/0064536 | A1 | 3/2018 | Brown et al. | |
| 2018/0318085 | A1 | 11/2018 | Felton et al. | |

FOREIGN PATENT DOCUMENTS

| | | | |
|---|---|---|---|
| WO | 2015093681 | A1 | 6/2015 |
| WO | 2017023041 | A1 | 2/2017 |

OTHER PUBLICATIONS

International Search Report and Written Opinion for Application No. PCT/US2019/060947, mailed on Apr. 22, 2020, 11 pages.

Communication under Rule 71(3) EPC for European Application No. 19836193.3, mailed Oct. 14, 2024, 52 pages.

Second Office Action for Chinese Application No. 201980074006.4 (with English translation), mailed Apr. 10, 2024, 18 pages.

* cited by examiner

206

224

600

BI-DIRECTIONAL VALVE PUMP

CROSS-REFERENCE TO RELATED APPLICATIONS

This application is a continuation of, and claims priority to, U.S. patent application Ser. No. 16/680,141, filed on Nov. 11, 2019, entitled "BI-DIRECTIONAL VALVE PUMP", which claims priority to U.S. patent application Ser. No. 62/768,406, filed on Nov. 16, 2018, entitled "BI-DIRECTIONAL VALVE PUMP", the disclosures of which are incorporated by reference herein in their entirety.

TECHNICAL FIELD

This disclosure relates generally to bodily implants and more specifically to bodily implants, such as penile prosthesis that includes a bi-directional valve pump.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. According to some existing designs of inflatable penile prostheses, the amount of time, energy and disparity from the occurrence of a normal human male erection for the patient to inflate a penile prosthesis (e.g., the number of pumps and time required to provide the desired penis rigidity) may be relatively high.

SUMMARY

According to an aspect, an inflatable penile prosthesis includes a fluid reservoir configured to hold fluid, an inflatable member, and a pump assembly configured to transfer the fluid between the fluid reservoir and the inflatable member. The pump assembly includes a valve body, a pump bulb, and a deflation mode actuator. The valve body includes a bi-directional valve configured to move from an inflation position to a deflation position in response to an activation of the deflation mode actuator. The bi-directional valve in the inflation position is configured to open a fluid passageway in the valve body to transfer fluid from the pump bulb to the inflatable member. The bi-directional valve in the deflation position is configured to open a fluid passageway in the valve body to transfer fluid from the inflatable member to the fluid reservoir that bypasses the pump bulb.

According to some aspects, the inflatable penile prosthesis may include one or more of the following features (or any combination thereof). The bi-directional valve may include a control valve ball configured to move between the inflation position and the deflation position. The bi-directional valve may include at least one pusher member operatively coupled to the deflation mode actuator, where the at least one pusher member is configured to cause the control valve ball to move to the deflation position. The at least one pusher member may include a first pusher member operatively coupled to a first deflation button, and a second pusher member operatively coupled to a second deflation button. Actuation of either the first deflation button or the second deflation button may cause the control valve ball to move to the deflation position. The deflation mode actuator may include a feedback component configured to provide at least one of tactile or auditory feedback in response to the activation of the deflation mode actuator. The valve body may include a first surface and a second surface opposite the first surface, and the deflation mode actuator may include a first deflation button extending from the first surface, and a second deflation button extending from the second surface. The pump assembly may include a plurality of fluid transfer ports that extend from the valve body, and the plurality of fluid transfer ports include a reservoir fluid port, a first cylinder fluid port, and a second cylinder fluid port. The valve body may include a refill valve aligned with the reservoir fluid port, where the refill valve is configured to transfer fluid from the fluid reservoir to the pump bulb when the bi-directional valve is in the inflation position. The valve body may include an inflation valve fluidly coupled to the pump bulb. The refill valve and the inflation valve are not used when the bi-directional valve is in the deflation position.

According to an aspect, a pump assembly for an inflatable penile prosthesis includes a valve body including a bi-directional valve, a plurality of fluid transfer ports extending from the valve body, where the plurality of fluid transfer ports include a reservoir fluid port and at least one cylinder fluid port, a pump bulb extending from the valve body, and a deflation mode actuator moveably coupled to the valve body. The bi-directional valve is configured to move from an inflation position to a deflation position in response to an activation of the deflation mode actuator. The bi-directional valve in the inflation position is configured to open a fluid passageway from the pump bulb to the at least one cylinder fluid port. The bi-directional valve in the deflation position is configured to open a fluid passageway from the reservoir fluid port to the at least one cylinder fluid port that bypasses the pump bulb.

According to some aspects, the pump assembly may include one or more of the above/below features (or any combination thereof). The deflation mode actuator may include a deflation button and a feedback component configured to provide at least one of tactile or auditory feedback in response to the deflation button being pressed by a user. The valve body may include a first surface and a second surface opposite the first surface, and the deflation mode actuator may include a first deflation button extending from the first surface, and a second deflation button extending from the second surface. The valve body may include a refill valve disposed in a fluid passageway between the reservoir fluid port and the pump bulb, where the refill valve is aligned along an axis that extends along a longitudinal axis of the reservoir fluid port, and the refill valve is configured to transfer fluid from the fluid reservoir to the pump bulb when the bi-directional valve is in the inflation position. The bi-directional valve may include a control valve ball and at least one pusher member operatively coupled to the deflation mode actuator, where the at least one pusher member is configured to cause the control valve ball to move to the deflation position. The deflation mode actuator may include a first deflation button extending from a first surface of the valve body, and a second deflation button extending from a second surface of the valve body. The at least one pusher member may include a first pusher member operatively coupled to the first deflation button, and a second pusher member operatively coupled to the second deflation button. The valve body may include a refill valve, and an inflation valve, where the refill valve and the inflation valve are not used when the bi-directional valve is in the deflation position.

According to an aspect, a method for controlling a direction of fluid through a pump assembly of an inflatable penile prosthesis includes transferring, by a pump assembly, fluid from a fluid reservoir to an inflatable member, including transferring the fluid from the fluid reservoir to a pump bulb via a refill valve and transferring the fluid from the pump bulb to the inflatable member via an inflation valve and a bi-directional valve. The method includes moving the bi-directional valve to a deflation position in response to activation of a deflation mode actuator, and transferring the fluid from the inflatable member to the fluid reservoir via the bi-directional valve such that the fluid is not transferred through the pump bulb. In some examples, the refill valve and the inflation valve are not used to transfer the fluid from the inflation member to the fluid reservoir when the bi-directional valve is in the deflation position.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1:
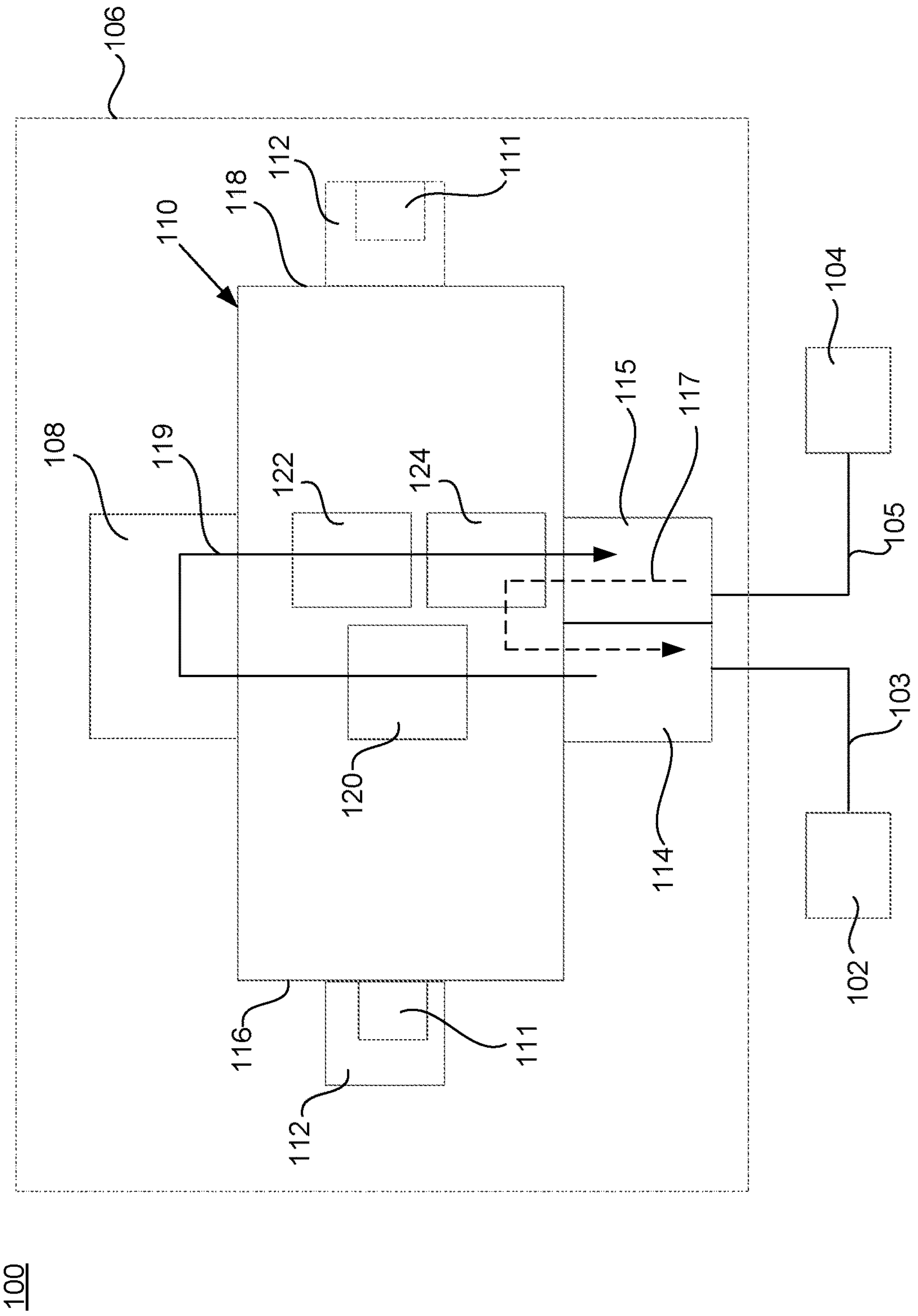
FIG. 1 illustrates an inflatable penile prosthesis including a fluid reservoir, an inflatable member, and a pump assembly configured to transfer fluid between the fluid reservoir and the inflatable member according to an aspect.

FIG. 1 illustrates an inflatable penile prosthesis 100 including a fluid reservoir 102, an inflatable member 104, and a pump assembly 106 configured to transfer fluid between the fluid reservoir 102 and the inflatable member 104 according to an aspect. The inflatable member 104 may be implanted into the corpus cavernosae of the user, the fluid reservoir 102 may be implanted in the abdomen or pelvic cavity of the user (e.g., the fluid reservoir 102 may be implanted in the lower portion of the user's abdominal cavity or the upper portion of the user's pelvic cavity), and the pump assembly 106 may be implanted in the scrotum of the user.

The pump assembly 106 includes a pump bulb 108, a valve body 110, a deflation mode actuator 112, and fluid transfer ports such as a reservoir fluid port 114 fluidly coupled to the fluid reservoir 102 (via a first conduit connector 103) and one or more cylinder fluid ports 115 fluidly coupled to the inflatable member 104 (via a second conduit connector 105). The fluid transfer ports may extend from an end portion of the valve body 110. In some examples, the fluid transfer ports are disposed on (or defined by) a fluid transfer member that is separate from the valve body 110, where the fluid transfer member is coupled to the valve body 110. In some examples, the reservoir fluid port 114 includes an elongated tubular member defining a cavity. In some examples, the cylinder fluid ports 115 includes a first cylinder fluid port fluidly connected to a first cylinder member of the inflatable member 104, and a second cylinder fluid port fluidly connected to a second cylinder member of the inflatable member 104. In some examples, the cylinder fluid ports 115 include elongated tubular members that define cavities.

The valve body 110 includes a bi-directional valve 124 configured to move from an inflation position to a deflation position in response to an activation of the deflation mode actuator 112. The bi-directional valve 124 may include a directional control valve and a movable component (e.g., ball, poppet, spool etc.) that moves between the inflation position and the deflation position with respect to the directional control valve in order to control the direction of the fluid through the fluid passageways of the valve body. In some examples, the bi-directional valve 124 includes a two-way two-position direction control valve. In some examples, the design of the bi-directional valve 124 may reduce (or eliminate) the possibility for the pump bulb 108 to get stuck in a collapsed state even if the first squeeze to switch from the deflation mode to the inflation mode does not successfully move the bi-directional valve 124 to the inflation position.

When the bi-directional valve 124 is in the inflation position, the inflatable penile prosthesis 100 is in an inflation mode (or inflation cycle). When the bi-directional valve 124 is in the deflation position, the inflatable penile prosthesis 100 is in a deflation mode (or deflation cycle). In some examples, a single, instantaneous push of the deflation mode actuator 112 transfers the bi-directional valve 124 to the deflation position (e.g., as opposed to holding the deflation mode actuator 112 for a certain predetermined time). In some examples, movement of the bi-directional valve 124 to the deflation position causes a fluid pathway (e.g., the dashed arrow 117 in FIG. 1) to open between the cylinder fluid ports 115 and the reservoir fluid port 114 such that fluid can be transferred from the inflatable member 104 back to the fluid reservoir 102 via the pump assembly 106 in a manner that bypasses the pump bulb 108.

In contrast, in the inflation mode, the pump bulb 108 is used to transfer fluid from the fluid reservoir 102 to the inflatable member 104 (e.g. the pump bulb 108 is not bypassed). For example, the user may depress (or squeeze) the pump bulb 108 and then release the pump bulb 108, and then repeat these operations until the desired rigidity is achieved in the inflatable member 104. As shown by the non-dashed arrow 119 in FIG. 1, the release of the pump bulb 108 creates a suction force that pulls fluid from the fluid reservoir 102 to the pump bulb 108, and the depression of the pump bulb 108 expels the fluid from the pump bulb 108 to the inflatable member 104. In some examples, in the inflation mode, the valve body 110 provides an optimized fluid passageway via the bi-directional valve 124 that may decrease the pressure drop across the bi-directional valve 124 for faster inflate time and/or decrease the fluid resistance thereby requiring less pump bulb squeeze force to inflate.

The pump bulb 108 may be a flexible member defining a cavity. The pump bulb 108 is coupled to and extends from the valve body 110. In some examples, the pump bulb 108 extends from the valve body 110 in a direction that is opposite to the direction in which the reservoir fluid port 114 and the cylinder fluid ports 115 extend from the valve body 110 (e.g., located on opposite ends of the valve body 110). The pump bulb 108 may be a squeeze pump. In some examples, the pump bulb 108 includes ribbing or dimples to aid the user in gripping the pump bulb 108. As indicated above, the pump bulb 108 may use suction and pressure to move the fluid in and out of the cavity of the pump bulb 108 in the inflation mode. For example, the user may depress or squeeze the pump bulb 108 to expel the fluid out of the cavity, and, when the flexible member returns to its original shape, the resulting suction pushes the fluid into the cavity of the pump bulb 108. In some examples, the pump bulb 108 may have a bulb spring rate that is designed to refill the pump bulb 108 in a selected time frame.

The valve body 110 defines one or more fluid passageways through the valve body 110 (e.g., between the reservoir fluid port 114 and the pump bulb 108, the pump bulb 108 and the cylinder fluid ports 115, and the cylinder fluid ports 115 and the reservoir fluid port 114). The valve body 110 includes valve components disposed within the fluid passageways to control the flow of the fluid through the valve body 110 in the inflation mode and the deflation mode. In some examples, the valve body 110 includes a block of material that defines the fluid passageways and encloses the valve components. In some examples, the valve body 110 includes a silicone material. In some examples, the valve body 110 may be molded from a silicone material having a medium durometer value. In some examples, the pump assembly 106 includes an outer protective casing that is disposed over the valve body 110. In some examples, the outer protective casing has a material (e.g., a polymer material) that is different from the valve body 110. In some examples, the outer protective casing includes one or more tactile features that help the user locate the valve body 110 (in order to locate the deflation mode actuator 112). In some examples, the tactile features include protruded portions, ridges, grooves, bumps, and/or depressions.

The valve body 110 includes the bi-directional valve 124, a refill valve 120, and an inflation valve 122. In some examples, the valve body 110 includes an anti-auto inflate valve. The refill valve 120 may be used when the pump bulb 108 is refilled. The refill valve 120 is not used in the deflation mode. In some examples, the refill valve 120 is a one-way valve. In some examples, the refill valve 120 is disposed in a fluid passageway within the valve body 110 between the reservoir fluid port 114 and the pump bulb 108. In some examples, the fluid passageway having the refill valve 120 that extends between the reservoir fluid port 114 and the pump bulb 108 is used only for refilling the pump bulb 108 (e.g., a separated fluid pathway), which may decrease bulb refill time (e.g., deceases the wait time between squeezes).

In some examples, the refill valve 120 is aligned with the reservoir fluid port 114. For example, the refill valve 120 may have an inlet and an outlet, where fluid enters the inlet from the reservoir fluid port 114 and exits the outlet to the pump bulb 108. The reservoir fluid port 114 may define a longitudinal axis that extends along the fluid pathway (e.g., between the inlet and the outlet) of the refill valve 120. The alignment of the refill valve 120 with the reservoir fluid port 114 may minimize fluid pathway tortuosity, and/or decrease pressure drop across the refill valve 120. In some examples, the refill valve 120 includes a floating check ball with fluting (which may increase or maximize fluid velocity across the refill valve 120). In some examples, the refill valve 120 includes a biasing member that biases the refill valve 120 to a sealing position. In some examples, the biasing member includes a spring. In some examples, the refill valve 120 does not include a biasing member.

The inflation valve 122 may be disposed within a fluid passageway between the pump bulb 108 and the cylinder fluid ports 115. The inflation valve 122 may be used during the inflation of the inflatable member 104 (e.g., when the fluid is transferred from the pump bulb 108 to the inflatable member 104). The inflation valve 122 is not used during the deflation mode. In some examples, the inflation valve 122 is a one-way valve. In some examples, the inflation valve 122 includes a check ball and a biasing member. The biasing member may bias the check ball to a sealing position. In some examples, the biasing member includes a spring. In some examples, the bi-directional valve 124 is disposed within a fluid passageway between the inflation valve 122 and the cylinder fluid ports 115. In some examples, the bi-directional valve 124 is aligned within the inflation valve 122.

In some examples, the bi-directional valve 124 includes a control valve ball that is configured to move from the inflation position to the deflation position (e.g., move in a linear direction). In some examples, the bi-directional valve 124 includes a poppet that is configured to move from the inflation position to the deflation position (and vice versa) (e.g., move in a linear direction). In some examples, the bi-directional valve 124 includes one or more pusher members operatively coupled to the deflation mode actuator 112. In some examples, the pusher members include cam pushers. In some examples, actuation of deflation mode actuator

112 causes the pusher member to move, which moves the control valve ball or poppet to the deflation position. In some examples, the pusher member moves in a direction orthogonal to the movement of the control valve ball or the poppet. In some examples, the bi-directional valve 124 includes a directional control valve (e.g., a rotating member, a swirl pot), where the pusher member moves (e.g., rotates) the directional control valve causing the control valve ball or the poppet to translate in a linear direction to the deflation position. In some examples, the directional control valve is a swirl pot. In some examples, the pusher members include a first pusher member operatively coupled to one deflation mode actuator 112, and a second pusher member operatively coupled to another deflation mode actuator 112. In some examples, in response to the deflation mode actuator 112 being pressed, the first pusher member moves within the valve body 110, contacts the swirl pot, and then rotates the swirl pot causing the control valve ball or the poppet to move to the deflation position. In response to the other deflation mode actuator 112 being pressed, the second pusher member moves within the valve body 110, contacts the swirl pot, and then rotates the swirl pot causing the control valve ball or the poppet to move to the deflation position.

In the inflation position (and when the user is operating the pump bulb 108), the fluid may flow from the reservoir fluid port 114 (from the fluid reservoir 102) to the pump bulb 108 via the refill valve 120, and from the pump bulb 108 to the cylinder fluid port 115 via the inflation valve 122 and the bi-directional valve 124 (and then to the inflatable member 104) as shown by the non-dashed arrow 119 of FIG. 1. Upon activation of the deflation mode actuator 112, the bi-directional valve 124 may open a fluid passageway in the valve body 110 to transfer fluid from the inflatable member 104 to the fluid reservoir that bypasses the pump bulb 108 as shown by the dashed arrow 117 of FIG. 1.

In some examples, when the control valve ball of the bi-directional valve 124 is in the deflation position, the refill valve 120 and the inflation valve 122 are not used (e.g., the refill valve 120 and the inflation valve 122 are bypassed as well). For example, movement of the bi-directional valve 124 from the inflation position to the deflation position causes a fluid passageway to open between the cylinder fluid ports 115 and the reservoir fluid port 114 such that fluid can be transferred through the valve body 110 in a manner that the pump bulb 108, the refill valve, and/or the inflation valve 122 are bypassed. In some examples, when the bi-directional valve 124 is in the deflation position, the bi-directional valve 124 directs the fluid flow from the cylinder fluid ports 115 to the reservoir fluid port 114. In some examples, upon actuation of the deflation mode actuator 112, the control valve ball of the bi-directional valve 124 moves from the inflation position to the deflation position (e.g., a linear direction towards the pump bulb 108).

The deflation mode actuator 112 is movably coupled to the valve body 110. In some examples, the deflation mode actuator 112 includes a deflation button, that when pressed, causes the control ball of the bi-directional valve 124 to move to the deflation position. In some examples, the deflation mode actuator 112 includes a push rod. In some examples, the user presses the deflation mode actuator 112 once (e.g., does not need to hold the deflation mode actuator 112) to cause fluid to drain from the inflatable member 104. In some examples, due to the pressure inside of the inflatable member 104, some of the fluid may be automatically transferred from the inflation member 104 to the fluid reservoir 102 via the pump assembly 106, and then the user may squeeze the inflatable member 104 to transfer some of the remaining fluid in the inflatable member 104.

In some examples, the valve body 110 includes multiple deflation mode actuators 112 on sides (or surfaces) of the valve body 110. For example, some users of conventional pump designs have experienced difficulties with locating the deflation button, which may cause patient frustration as well as increased training time for the physician, and in some cases, prolonged erections for those patients that need medical intervention to press the deflation button and release fluid from the cylinders.

However, in some examples, one deflation mode actuator 112 may be disposed on (or extending from) a first surface 116 of the valve body 110, and another deflation mode actuator 112 may be disposed on (or extending from) a second surface 118 of the valve body 110, where the second surface 118 is disposed opposite to the first surface 116. A user may press either of the deflation mode actuators 112 to place the bi-directional valve 124 in the deflation position (e.g., each may independently cause the bi-directional valve 124 to be placed in the deflation position).

In some examples, the valve body 110 includes more than two deflation mode actuators 112. In some examples, a separate deflation mode actuator 112 may exist on each of the four side surfaces of the valve body 110. For example, the valve body 110 may be a valve block, where the pump bulb 108 extends from one end surface, and the fluid transfer ports extends from the other end surface, and each of the four surfaces between the end surfaces include a separate deflation mode actuator 112 (e.g., a first deflation button, a second deflation button, a third deflation button, and a fourth deflation button). In some examples, the deflation mode actuators 112 can independently cause the bi-directional valve 124 to move to the deflation position. With the design of the bi-directional valve 124, the user has more flexibility in the way the deflation mode actuators 112 are manually located and actuated. In addition, the pump assembly 106 has the potential to rotate in the scrotum post implantation, which may be another benefit of having deflation mode actuators 112 on multiple different sides (e.g., 2 or 4 different sides) of the valve body 110.

In some examples, the deflation mode actuator 112 includes a feedback component 111 configured to provide at least one of tactile or auditory feedback in response to the activation of the deflation mode actuator 112. For example, when the deflation mode actuator 112 is pressed, the feedback component 111 may provide a sound and/or tactile feeling that the inflatable penile prosthesis 100 has entered the deflation mode. In some examples, the feedback component 111 is located between the deflation button and a pusher member, and when the feedback component 111 is compressed, the feedback component 111 is configured to provide tactile and/or auditory feedback indicating that the inflatable penile prosthesis 100 has entered the deflation mode. In some examples, the feedback component 111 includes a dome component.

Each of the first conduit connector 103 and the second conduit connector 105 may define a lumen configured to transfer the fluid to and from the pump assembly 106. The first conduit connector 103 may be coupled to the pump assembly 106 and the fluid reservoir 102 such that fluid can be transferred between the pump assembly 106 and the fluid reservoir 102 via the first conduit connector 103. For example, the first conduit connector 103 may define a first lumen configured to transfer fluid between the pump assembly 106 and the fluid reservoir 102. The first conduit connector 103 may include a single or multiple tube members for transferring the fluid between the pump assembly 106 and the fluid reservoir 102.

The second conduit connector 105 may be coupled to the pump assembly 106 and the inflatable member 104 such that fluid can be transferred between the pump assembly 106 and the inflatable member 104 via the second conduit connector 105. For example, the second conduit connector 105 may define a second lumen configured to transfer fluid between the pump assembly 106 and the inflatable member 104. The second conduit connector 105 may include a single or multiple tube members for transferring the fluid between the pump assembly 106 and the inflatable member 104. In some examples, the first conduit connector 103 and the second conduit connector 105 may include a silicone rubber material. In some examples, the pump assembly 106 may be directly connected to the fluid reservoir 102.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of inflatable cylinders or at least two cylinders, e.g., a first cylinder member and a second cylinder member. The volumetric capacity of the inflatable member 104 may depend on the size of the inflatable cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The fluid reservoir 102 may include a container having an internal chamber configured to hold or house fluid that is used to inflate the inflatable member 104. The volumetric capacity of the fluid reservoir 102 may vary depending on the size of the inflatable penile prosthesis 100. In some examples, the volumetric capacity of the fluid reservoir 102 may be 3 to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 contains a larger volume of fluid than the inflatable member 104.

FIGS. 2A through 2G illustrate various perspectives of a pump assembly 206 having a bi-directional valve 224 configured to move from an inflation position to a deflation position to open a fluid passageway that transfers fluid from an inflatable member to a fluid reservoir in a manner that bypasses a pump bulb 208. In some examples, the pump assembly 206 is an example of the pump assembly 106, and may include any of the features discussed with reference to the inflatable penile prosthesis 100 of FIG. 1.

Figure 2A:
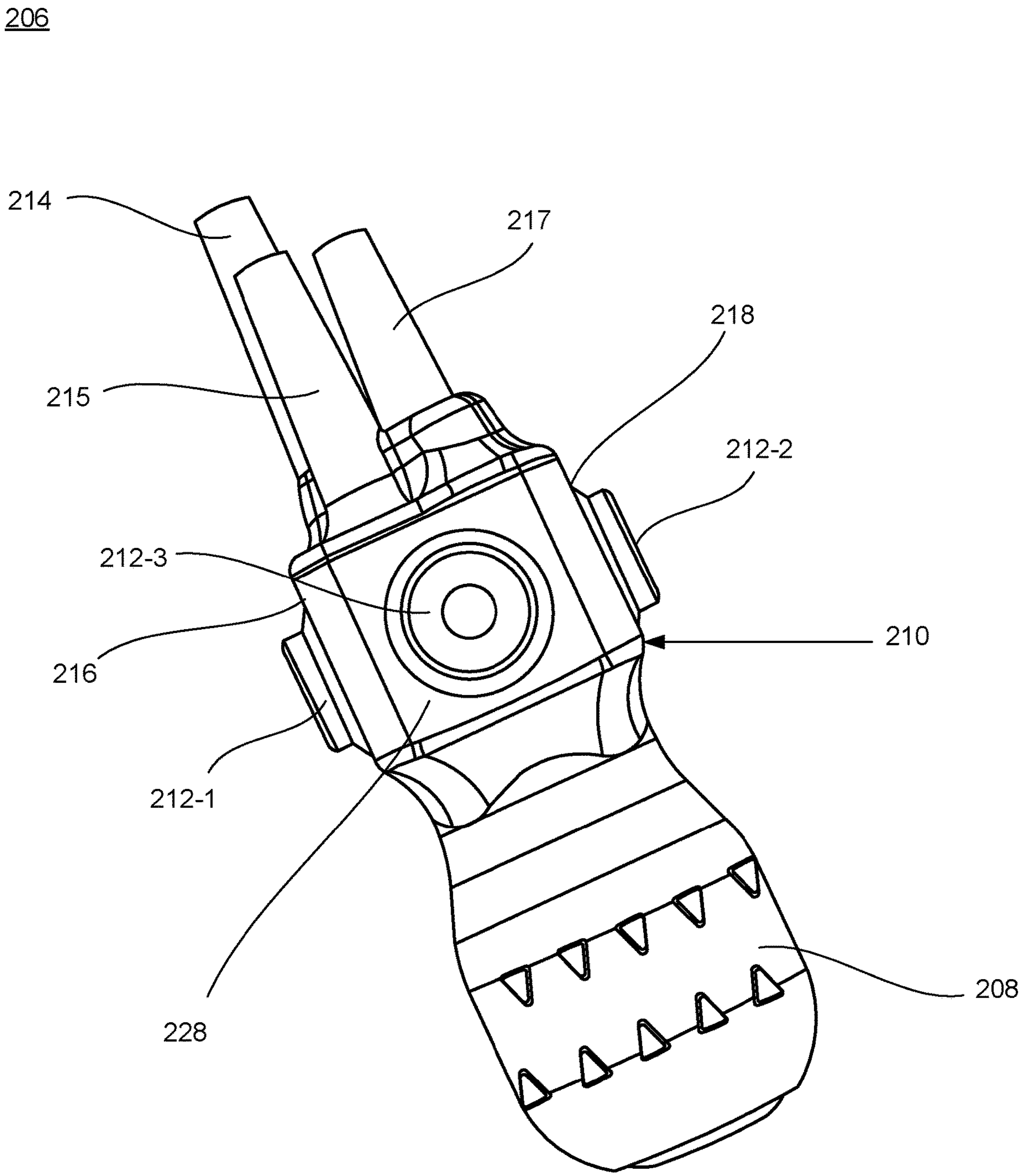
FIG. 2A illustrates the pump assembly according to an aspect.
Figure 2B:
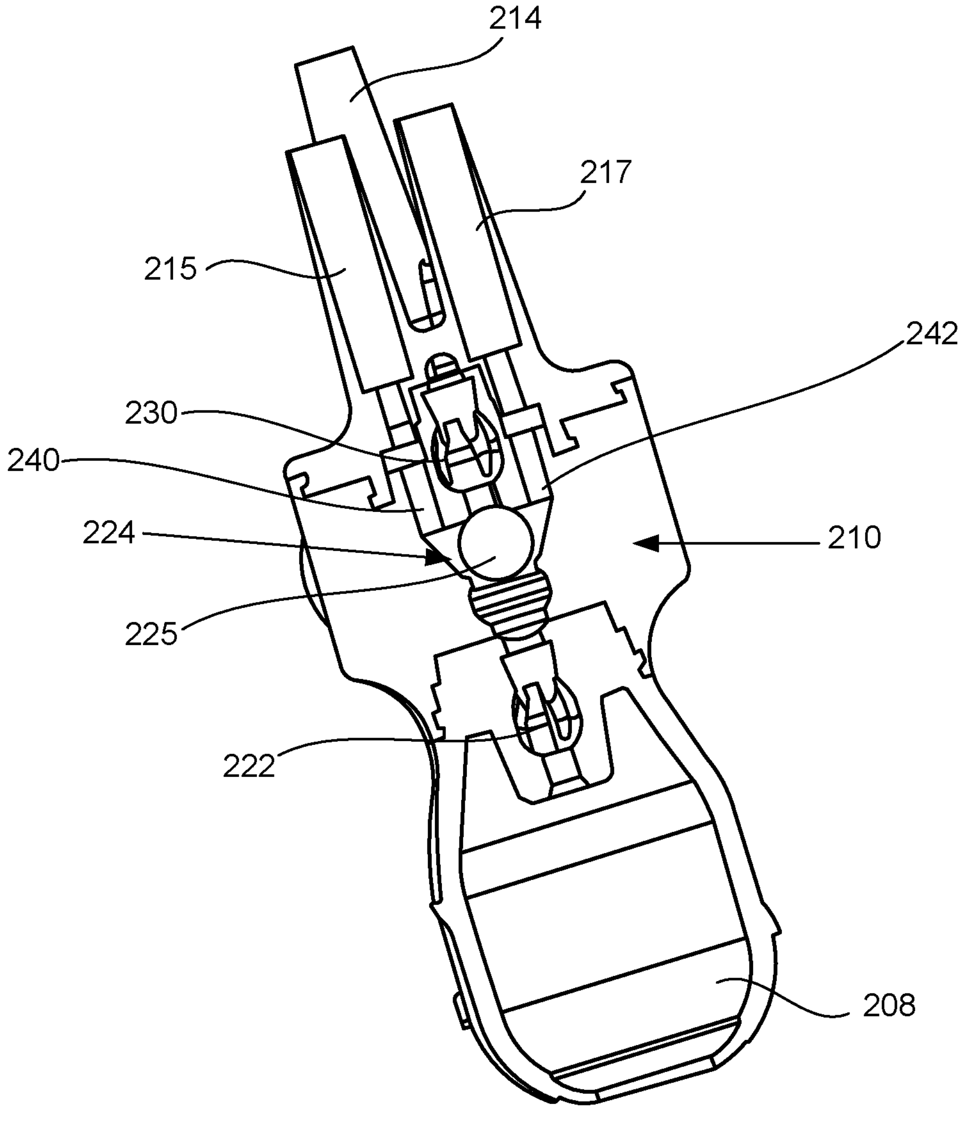
FIG. 2B illustrates a perspective of the pump assembly having a bi-directional valve in an inflation position according to an aspect.
Figure 2C:
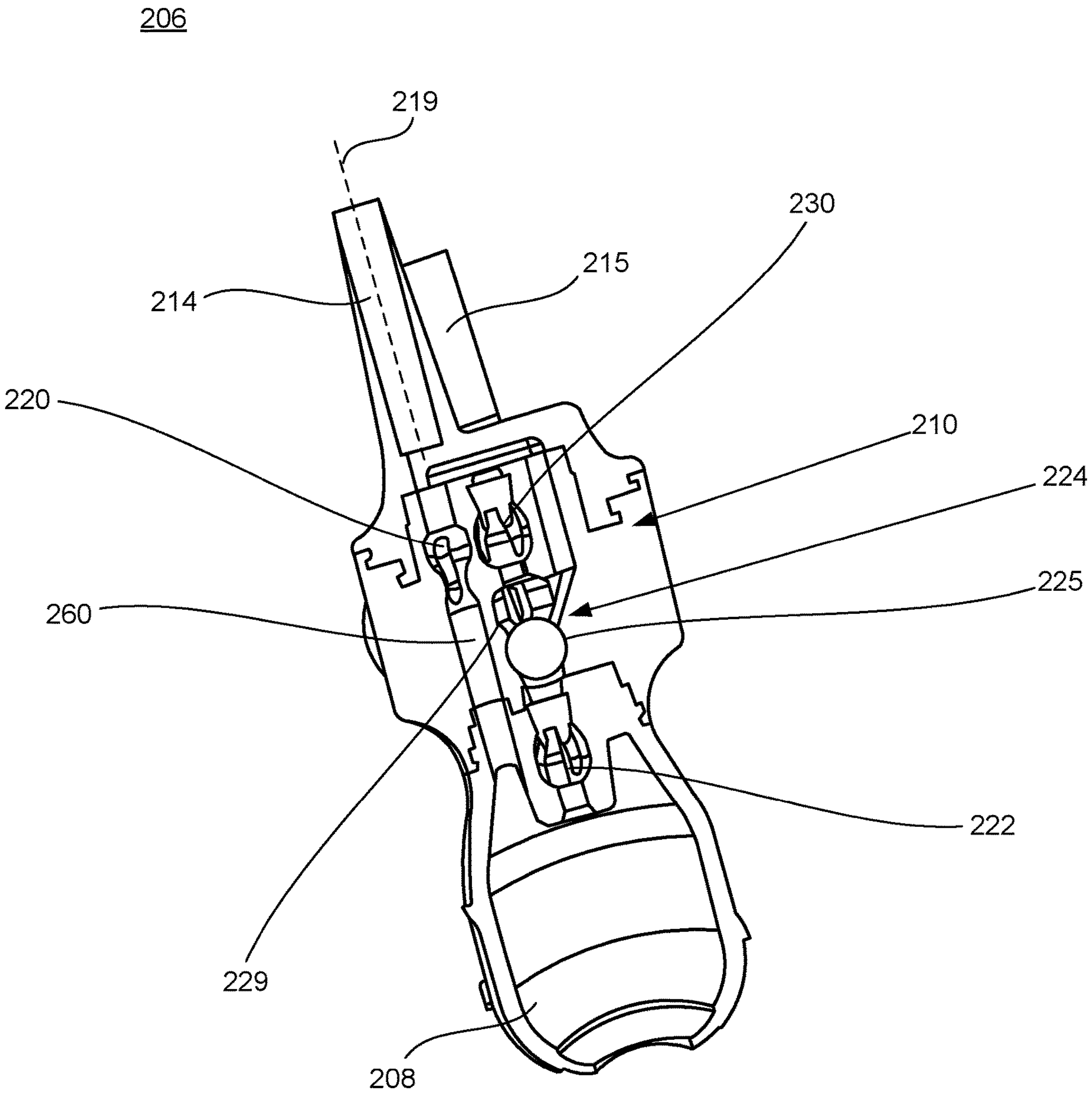
FIG. 2C illustrates a perspective of the pump assembly having the bi-directional valve in a deflation position according to an aspect.
Figure 2D:
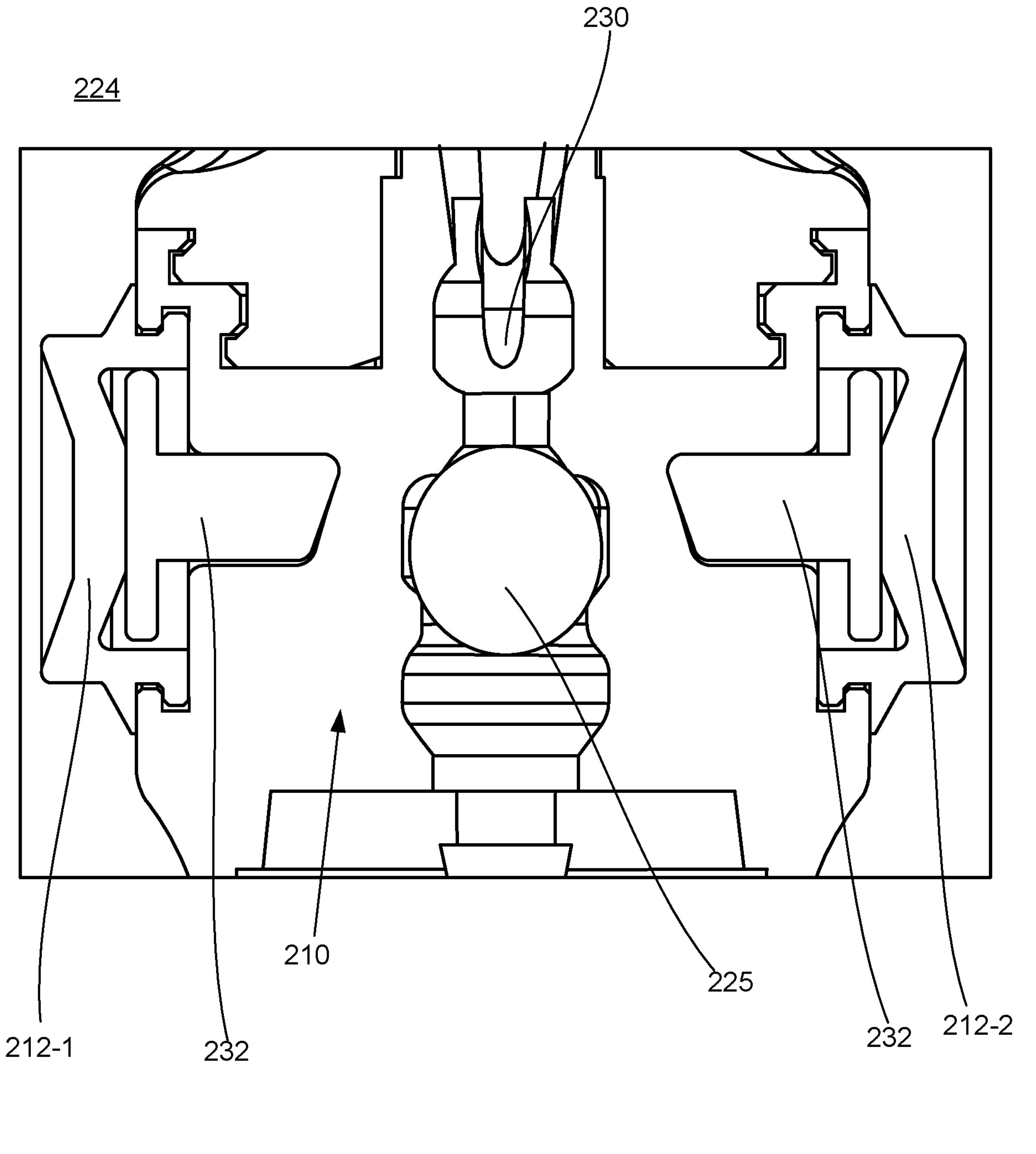
FIG. 2D illustrates a first cross-section of the bi-directional valve according to an aspect.
Figure 2E:
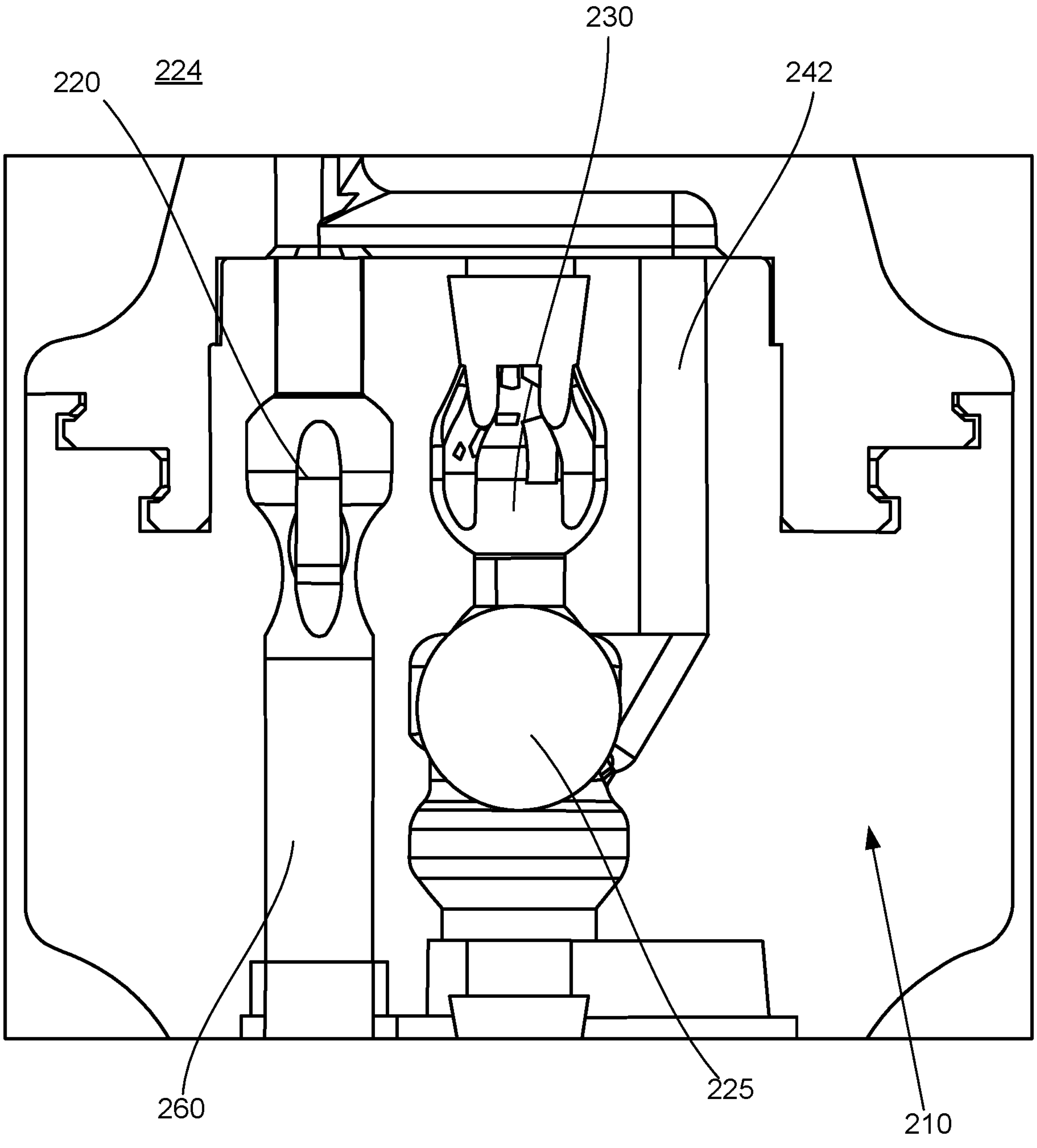
FIG. 2E illustrates a second cross-section of the bi-directional valve according to an aspect.
Figure 2F:
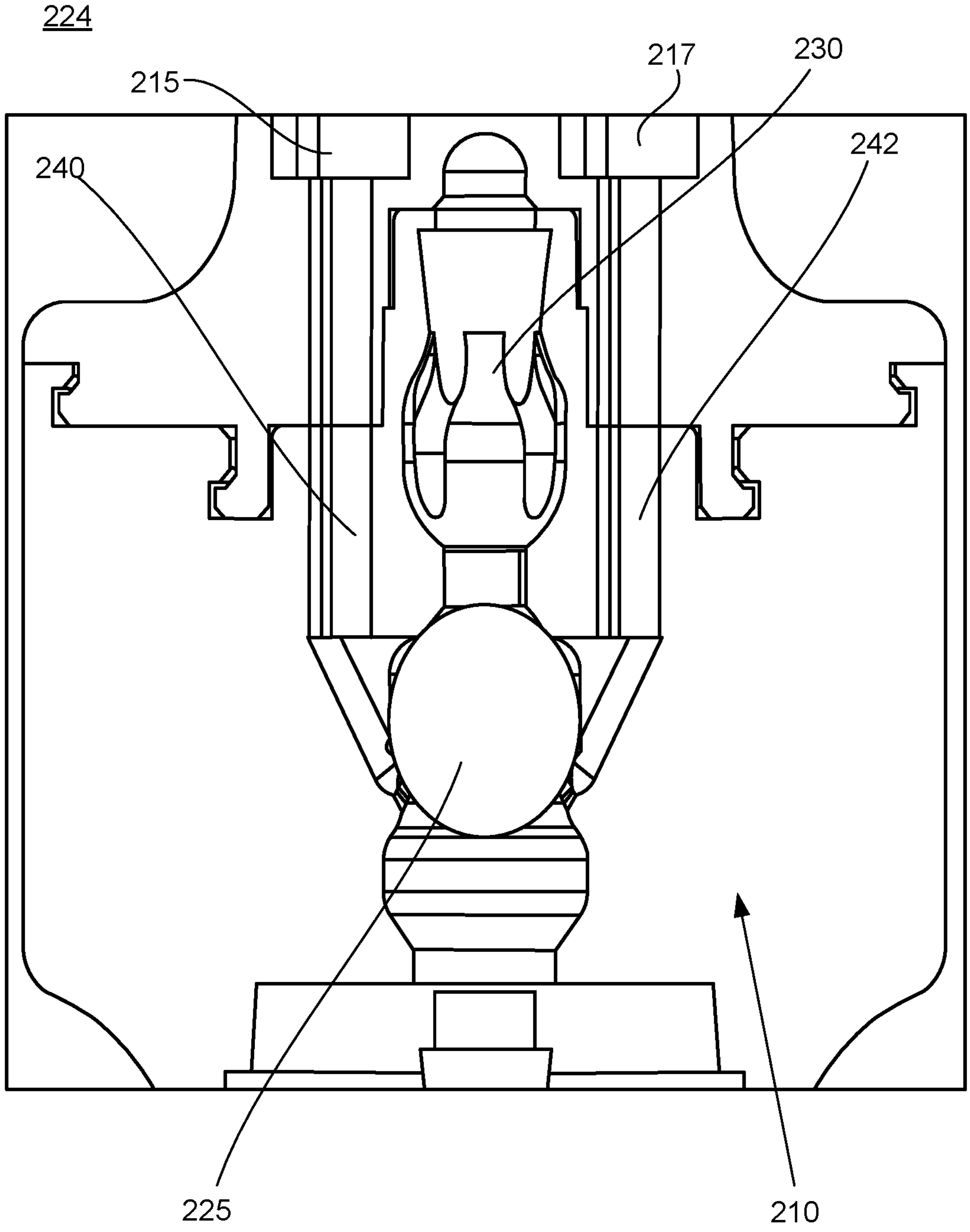
FIG. 2F illustrates a third cross-section of the bi-directional valve according to an aspect.
Figure 2G:
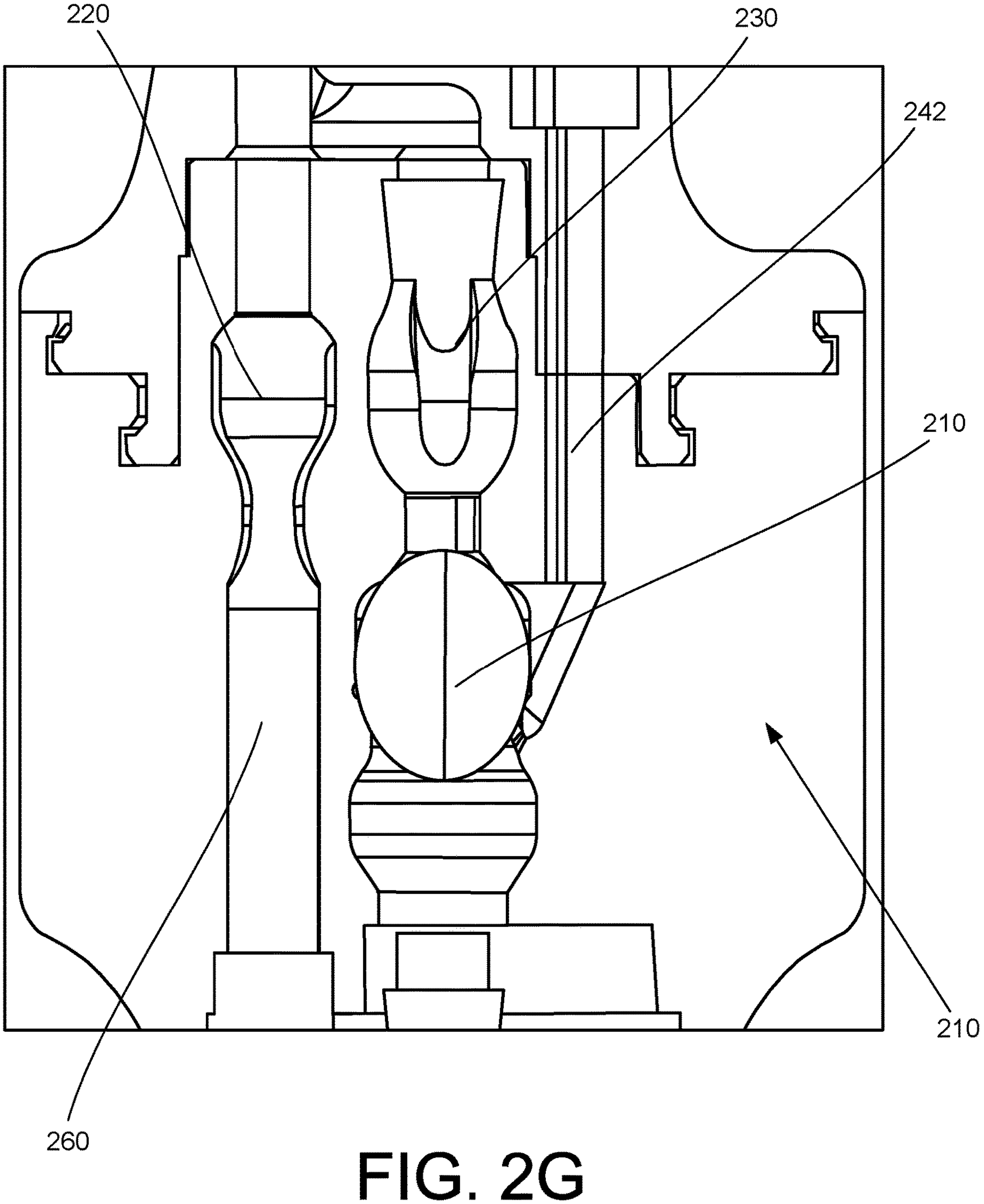
FIG. 2G illustrates a double cross-section of the bi-directional valve according to an aspect.

FIG. 2A illustrates the pump assembly 206 according to an aspect. FIG. 2B illustrates a perspective of the pump assembly 206 having the bi-directional valve 224 in an inflation position according to an aspect. FIG. 2C illustrates a perspective of the pump assembly 206 having the bi-directional valve 224 in a deflation position according to an aspect. FIG. 2D illustrates a first cross-section of the bi-directional valve 224 according to an aspect. FIG. 2E illustrates a second cross-section of the bi-directional valve 224 according to an aspect. FIG. 2F illustrates a third cross-section of the bi-directional valve 224 according to an aspect. FIG. 2G illustrates a double cross-section of the bi-directional valve 224 according to an aspect.

The pump assembly 206 includes a valve body 210, the pump bulb 208, deflation buttons such as a first deflation button 212-1, a second deflation button 212-2, a third deflation button 212-3, and a fourth deflation button (not shown), and fluid ports such as a first cylinder fluid port 215, a second cylinder fluid port 217, and a reservoir fluid port 214. In some examples, the pump bulb 208 extends from the valve body 210 in a first direction, and the fluid transfer ports extend from the valve body 210 in a second direction, where the second direction is opposite to the first direction. For example, the pump bulb 208 and the fluid transfer ports may extend on opposite ends of the valve body 210.

The reservoir fluid port 214 is configured to be connected to the first conduit connector 103 of FIG. 1, and the first cylinder fluid port 215 and the second cylinder fluid port 217 are configured to be connected to the second conduit connector 105 of FIG. 1. The first cylinder fluid port 215 may include a first tubular member defining a cavity. The second cylinder fluid port 217 may include a second tubular member defining a cavity. The reservoir fluid port 214 may include a third tubular member defining a cavity. In some examples, the first tubular member, the second tubular member, and the third tubular member are disposed parallel to each other. In some examples, the third tubular member (e.g., the reservoir fluid port 214) has a length longer than a length of the second tubular member and/or a length of the first tubular member.

The valve body 210 includes a first surface 216 and a second surface 218 disposed opposite to the first surface 216. For example, the first surface 216 and the second surface 218 may be disposed on opposite sides of the valve body 210. The first deflation button 212-1 may be disposed on (or extending from) the first surface 216 of the valve body 210. The second deflation button 212-2 may be disposed on (or extending from) the second surface 218 of the valve body 210. The valve body 210 includes a third surface 228 and a fourth surface (not shown) disposed opposite to the third surface 228. For example, the third surface 228 and the fourth surface may be disposed on opposite sides of the valve body 210. The third deflation button 212-3 may be disposed on (or extending from) the third surface 228 of the valve body 210. The fourth deflation button may be disposed on (or extending from) the fourth surface of the valve body 210.

A user may press one or more than one of the first deflation button 212-1, the second deflation button 212-2, the third deflation button 212-3, and the fourth deflation button to move the bi-directional valve 224 to the deflation position. In some examples, a single instantaneous push of one of the deflation buttons causes the bi-directional valve 224 to move to the deflation position. In some examples, the user presses two opposing deflation buttons (e.g., the first deflation button 212-1 and the second deflation button 212-2, or the third deflation button 212-3 and the fourth deflation button) to cause the bi-directional valve 224 to move to the deflation position.

The valve body 210 includes the bi-directional valve 224, a refill valve 220, an inflation valve 222, and an anti-auto inflate valve 230. In some examples, the refill valve 120 is disposed in a fluid passageway 260 within the valve body 210 between the reservoir fluid port 214 and the pump bulb 208 (shown in FIG. 2C). In some examples, the fluid passageway 260 is a passageway that is dedicated to only refilling the pump bulb 208 (e.g., not used to transfer fluid to the inflatable member or during deflation). For example, with respect to a pump refilling operation, the releasing of the pump bulb 208 causes a suction force that pulls the fluid from the fluid reservoir, through the reservoir fluid port 214, and through the valve body 210. In the valve body 210, the fluid is transferred along the fluid passageway 260 via the refill valve 120 to the pump bulb 208. In some examples, the refill valve 220 is aligned with the reservoir fluid port 214. The reservoir fluid port 214 may define a longitudinal axis 219 that is aligned with the refill valve's fluid passageway. The alignment of the refill valve 220 with the reservoir fluid port 214 may minimize fluid pathway tortuosity, and/or decrease pressure drop across the refill valve 220. In some examples, the refill valve 220 includes a floating check ball with fluting (which may increase or maximize fluid velocity across the refill valve 120).

The inflation valve 222 may be disposed in a fluid passageway that extends from (and/or or proximate to) to the pump bulb 208. In some examples, the inflation valve 222 includes a check ball and a biasing member. In examples, the biasing member includes a spring. In some examples, the bi-directional valve 224 is aligned with the inflation valve 222. In some examples, the anti-auto inflate valve 230 is aligned the bi-directional valve 224. In some examples, the bi-directional valve 224 is disposed between the anti-auto inflate valve 230 and the inflation valve 222.

The bi-directional valve 224 may include a control valve ball 225, a swirl pot 229, and pusher members 232. The control valve ball 225 may linearly move between the inflation position (as shown in FIG. 2B) and the deflation position (as shown in FIG. 2C). The pusher members 232 are coupled to the deflation buttons. In some examples, one pusher member 232 is coupled to a respective deflation button. For example, the first deflation button 212-1 is coupled to one pusher member 232, the second deflation button 212-2 is coupled to another pusher member 232, the third deflation button 212-3 is coupled to another pusher member 232, and the fourth deflation button is coupled to another pusher member 232. Upon activation of one of the deflation buttons, the corresponding pusher member 232 may move causing the swirl pot 229 to rotate to move the control valve ball 225 to the deflation position (e.g., the control valve ball 225 moves in a direction towards the pump bulb 208). In some examples, the pusher members 232 move in a direction orthogonal (e.g., perpendicular) to a direction in which the control valve ball 225 moves. In order to switch back to the inflation mode, the user may squeeze the pump bulb 208 that creates a pressure force that forces the control valve ball 225 to move back to the inflation position, thereby rotating the swirl pot 229 in the opposite direction.

In the inflation mode (as shown in FIG. 2B), the user squeezes the pump bulb 208 to transfer fluid from the pump bulb 208 to the first cylinder fluid port 215 and the second cylinder fluid port 217 via the valve body 210. In the inflation mode, the control valve ball 225 is in the inflation position. The fluid travels from the pump bulb 208, through the inflation valve 122, and the control valve ball 225 (in the inflation position) causes the fluid to flow through a fluid passageway 240 to the first cylinder fluid port 215 and through a fluid passageway 242 to the second cylinder fluid port 217. This fluid passageway (e.g., the fluid pathways from the pump bulb 108 to the cylinder fluid ports 215, 217) may decrease the pressure drop across the bi-directional valve 224 for faster inflate time, and reduce the amount of fluid resistance thereby requiring less pump bulb squeeze force. In the inflation mode, the anti-auto inflate valve 230 is not used. Then, the user releases the pump bulb 208, which causes the refilling operation as described above with respect to the refill valve 220. The user repeats these operations until a desired rigidity is achieved in the inflatable member.

In order to switch to the deflation mode, the user locates and presses one or more of the deflation buttons, which causes a particular pusher member 232 to move, thereby forcing the control valve ball 225 to the deflation position, as shown in FIG. 2C. For example, the pusher member 232 may rotate the swirl pot 229 causing the control valve ball 225 to move to the deflation position (e.g., the control valve ball 225 moves in a direction towards the pump bulb 208). In the deflation mode, the fluid is transferred from the inflatable member back to the fluid reservoir. For example, the fluid enters the first and second cylinder fluid ports 215, 217, and travels through the valve body 210 to the reservoir fluid port 214. In the valve body 210, the control valve ball 225 of the bi-directional valve 224 directs the fluid through the anti-auto inflate valve 230 to the reservoir fluid port 214. In contrast to the inflation mode (or cycle), this fluid passageway bypasses the pump bulb 208. Also, the refill valve 220 and the inflation valve are not used in the deflation mode.

Figure 3:
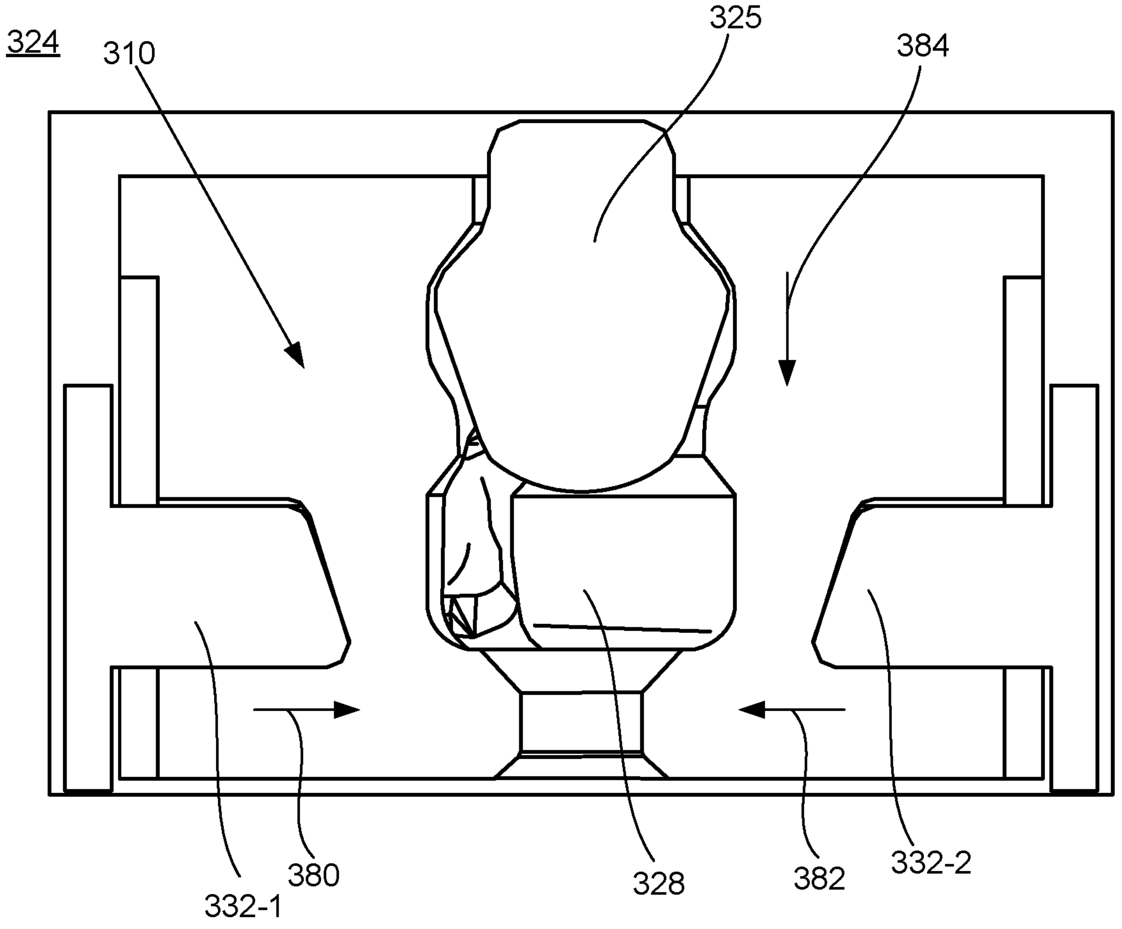
FIG. 3 illustrates a cross-section of a bi-directional valve according to another aspect.

FIG. 3 illustrates a cross-section of a bi-directional valve 324 according to an aspect. The bi-directional valve 324 may be similar to the bi-directional valve 224 and the bi-directional valve 124 (and may include any of the features discussed herein), but the bi-directional valve 324 includes a poppet 325 (instead of a control valve ball) disposed within a valve body 310. For example, the bi-directional valve 324 includes a swirl pot 328, and the poppet 325 is movable with respect to the swirl pot 328. In FIG. 3, the poppet 325 is in the inflation position. The bi-directional valve 324 includes a first pusher member 332-1 (coupled to a first deflation button), and a second pusher member 332-2 (coupled to a second deflation button). When the first deflation button is pressed, the first pusher member 332-1 moves towards the swirl pot 328 in a direction 380, contacts the swirl pot 328, and then rotates the swirl pot 328 causing the poppet 325 to move in a direction 384. In some examples, the direction 384 is orthogonal (e.g., perpendicular) to the direction 380. When the second deflation button is pressed, the second pusher member 332-2 moves towards the swirl pot 328 in a direction 382, contacts the swirl pot 328, and then rotates the swirl pot 328 causing the poppet 325 to move in the direction 384. In some examples, the direction 384 is orthogonal (e.g., perpendicular) to the direction 382. In some examples, the direction 382 is parallel (but opposite) to the direction 380.

Figure 4A:
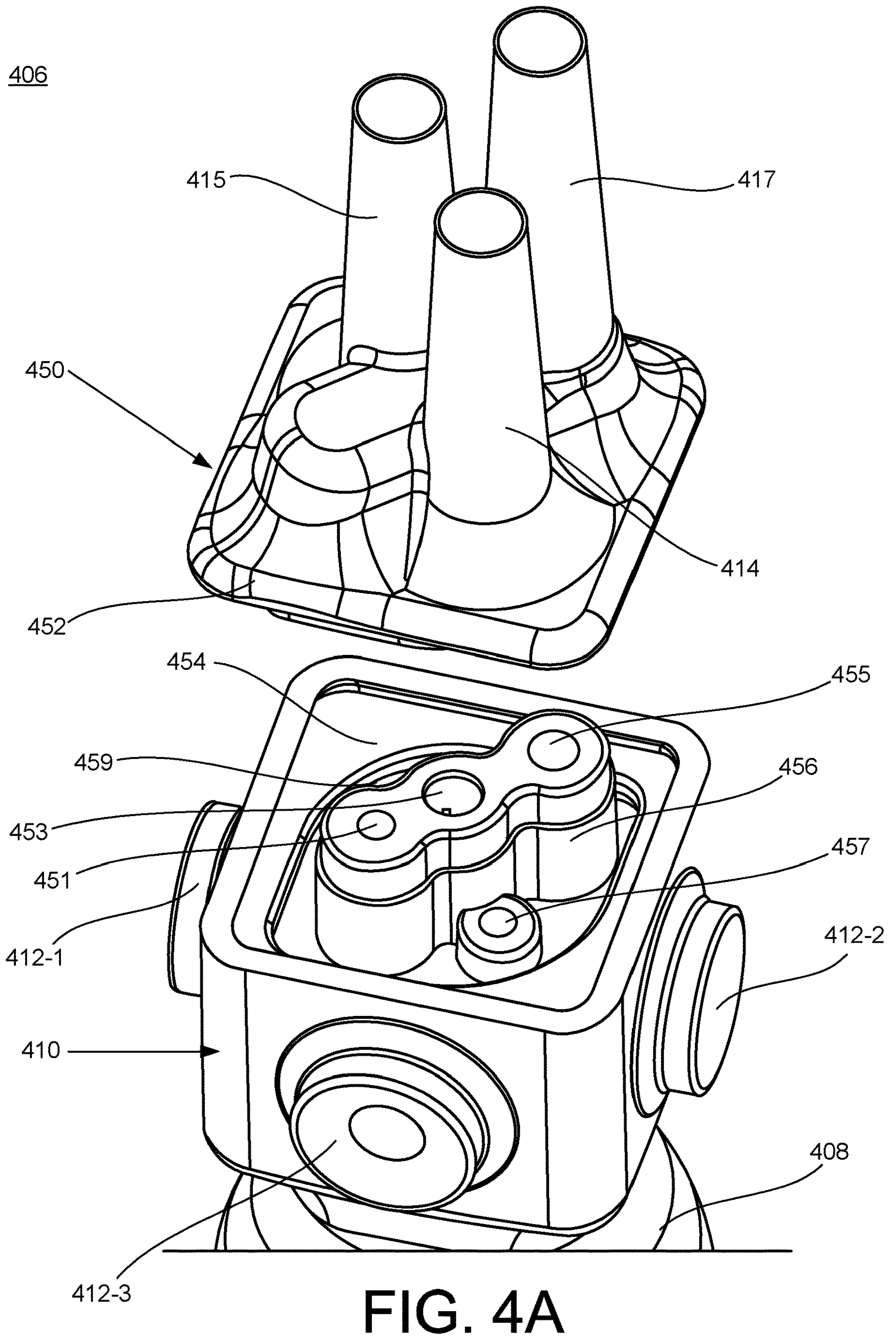
FIG. 4A illustrates a perspective of a pump assembly according to an aspect.
Figure 4B:
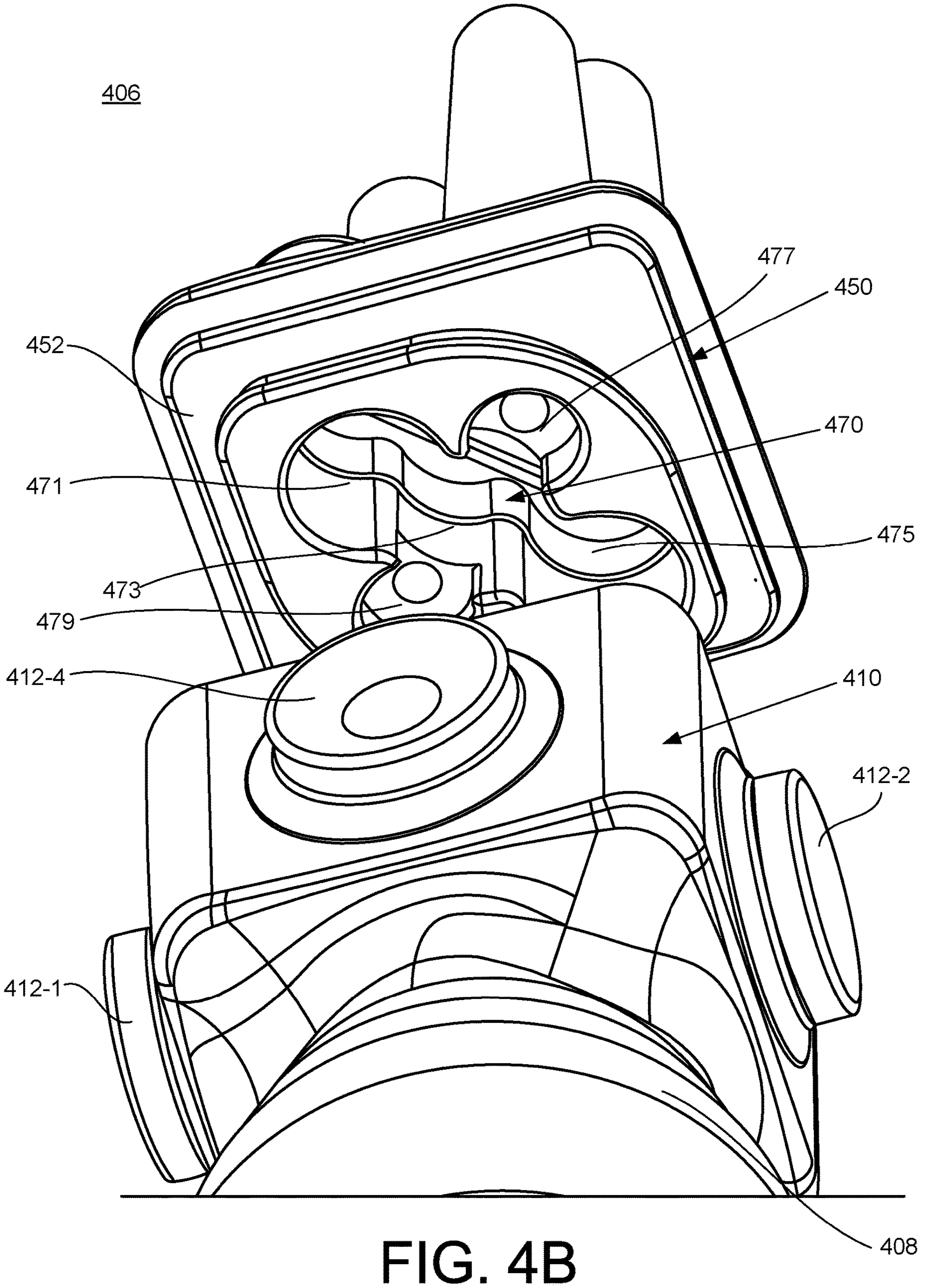
FIG. 4B illustrates a perspective of the pump assembly of FIG. 4A according to another aspect.

FIGS. 4A and 4B illustrate various perspectives of a pump assembly 406 according to an aspect. FIG. 4A illustrates a perspective of the pump assembly 406 according to an aspect. FIG. 4B illustrates a perspective of the pump assembly 406 according to another aspect. The pump assembly 406 may include any of the features described with reference to the previous figures. In some examples, the pump assembly 406 includes a fluid port member 450 that is separate from the valve body 410. However, the fluid port member 450 is coupled to the valve body 410. In some examples, the fluid port member 450 is coupled to the valve body 410 based on an interference fit. In some examples, the fluid port member 450 and the valve body 410 are coupled together using fasteners and/or a bonding material.

The fluid port member 450 includes a first cylinder fluid port 415, a second cylinder fluid port 417, and a reservoir fluid port 414. Also, the fluid port member 450 includes a base 452. The base 452 may be the foundational part or edge of the fluid port member 450 (e.g., the part on which it is supported). In some examples, the base 452 has a rectangular shape (with curved corners). However, the base 452 may include other shapes such as circular or non-circular shapes. The valve body 410 includes a base 454. The base 454 of the valve body 410 may have a shape/structure that corresponds to the shape/structure of the base 452. In some examples, the base 454 has a rectangular shape. However, the base 454 may include other shapes such as circular or non-circular shapes. The base 452 of the fluid port member 450 and the base 454 of the valve body 410 are configured to be coupled to each other.

The pump assembly 406 includes a pump bulb 408 that extends from the valve body 410 at a location opposite to the base 454. The valve body 410 includes a first deflation button 412-1, a second deflation button 412-2, a third deflation button 412-3, and a fourth deflation button 412-4 that are disposed on (or extending from) different side surfaces of the valve body 410.

As shown in FIG. 4A, the base 454 includes a raised portion 456 that defines a first opening 451, a second opening 453, and a third opening 455. The first opening 451, the second opening 453, and the third opening 455 extend into the valve body 410. Also, the base 454 includes a first protrusion that defines a fourth opening 457 and a second protrusion that defines a fifth opening 459. The raised portion 456 may be disposed between the fourth opening 457 and the fifth opening 459. In some examples, the first opening 451, the second opening 453, the third opening 455, the fourth opening 457, and the fifth opening 459 may be disposed parallel to each other.

As shown in FIG. 4B, at a location underneath the base 452, the base 452 defines a cavity 470 having shapes that correspond to the shapes of the raised portion 456, the first protrusion that defines the fourth opening 457, and the second protrusion that defines the fifth opening 459. For example, the cavity 470 includes a first cavity section 471, a second cavity section 473, and a third cavity section 475, which are configured to receive the raised portion 456 defining the first opening 451, the second opening 453, and the third opening 455, respectively. Also, the cavity includes a fourth cavity section 477 and a fifth cavity section 479, which are configured to receive the first protrusion that defines the fourth opening 457 and the second protrusion that defines the fifth opening 459.

Figure 5A:
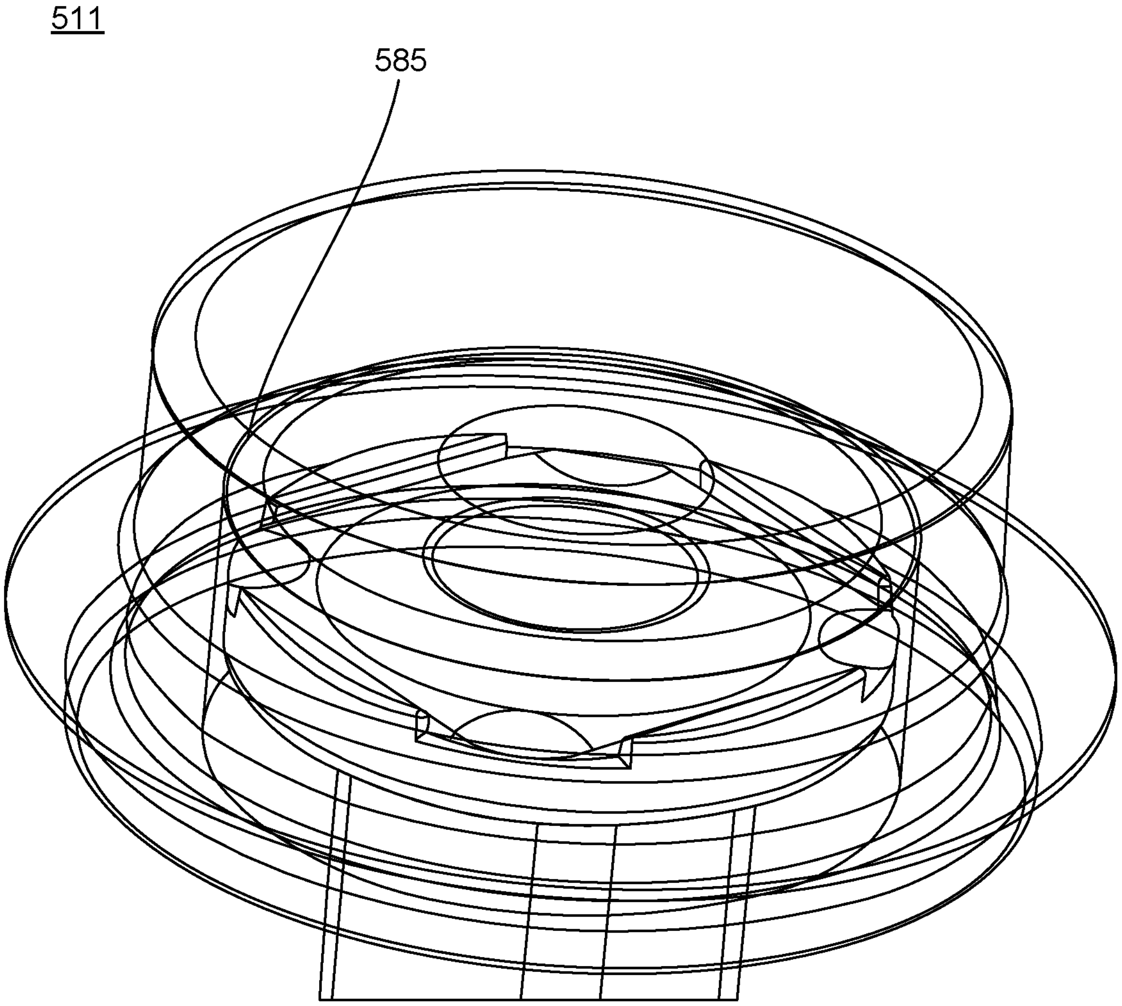
FIG. 5A illustrates a feedback component as a dome structure according to an aspect.
Figure 5B:
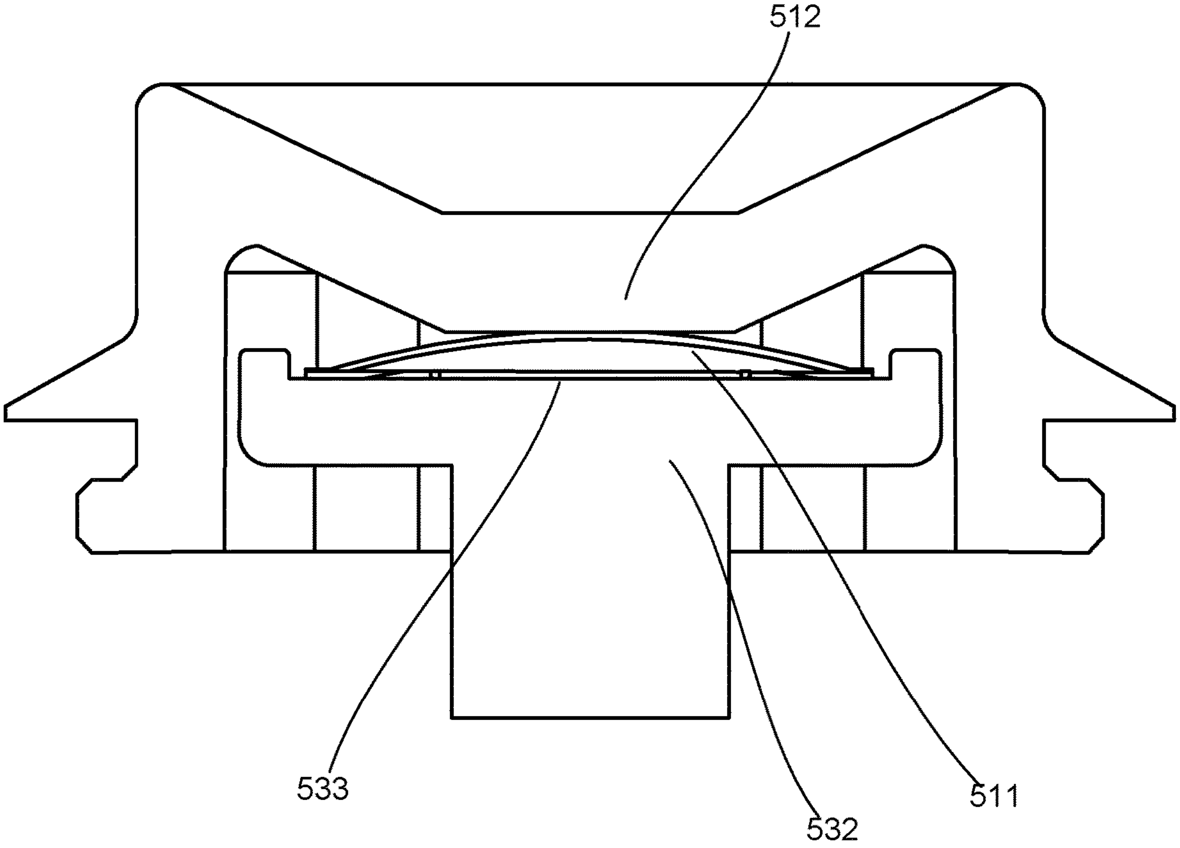
FIG. 5B illustrates the feedback component disposed between a deflation button and a pusher member according to an aspect.

FIGS. 5A through 5B illustrates various perspectives of a feedback component 511 configured to provide at least one of tactile or auditory feedback in response to the activation of a deflation button 512 according to an aspect. FIG. 5A illustrates the feedback component 511 as a dome structure 585 according to an aspect. In some examples, the dome structure 585 includes a rounded vault and a circular base. In some examples, when the dome structure 585 is compressed, the dome structure 585 may create a sound. In some examples, when the dome structure 585 is compressed, the dome structure 585 may provide a tactile sensation that is perceptible by the user. For example, the feedback component 511 may be integrated with the deflation button 512 such that when the user presses the deflation button 512, the feedback component 511 may provide a sound and/or tactile sensation that inform the user that the inflatable penile prosthesis is on the deflation mode.

FIG. 5B illustrates the feedback component 511 disposed on an end surface 533 of a pusher member 532 according to an aspect. When the deflation button 512 is pressed, the deflation button 512 moves the pusher member 532 in order to place the bi-directional valve in the deflation position. When the bi-direction valve is in the deflation position, the pusher member 532 is prevented from further movement, and the pusher member 532 and the deflation button 512 compress the feedback component 511, which causes the feedback component 511 to provide at least one of tactile or auditory feedback.

Figure 6:
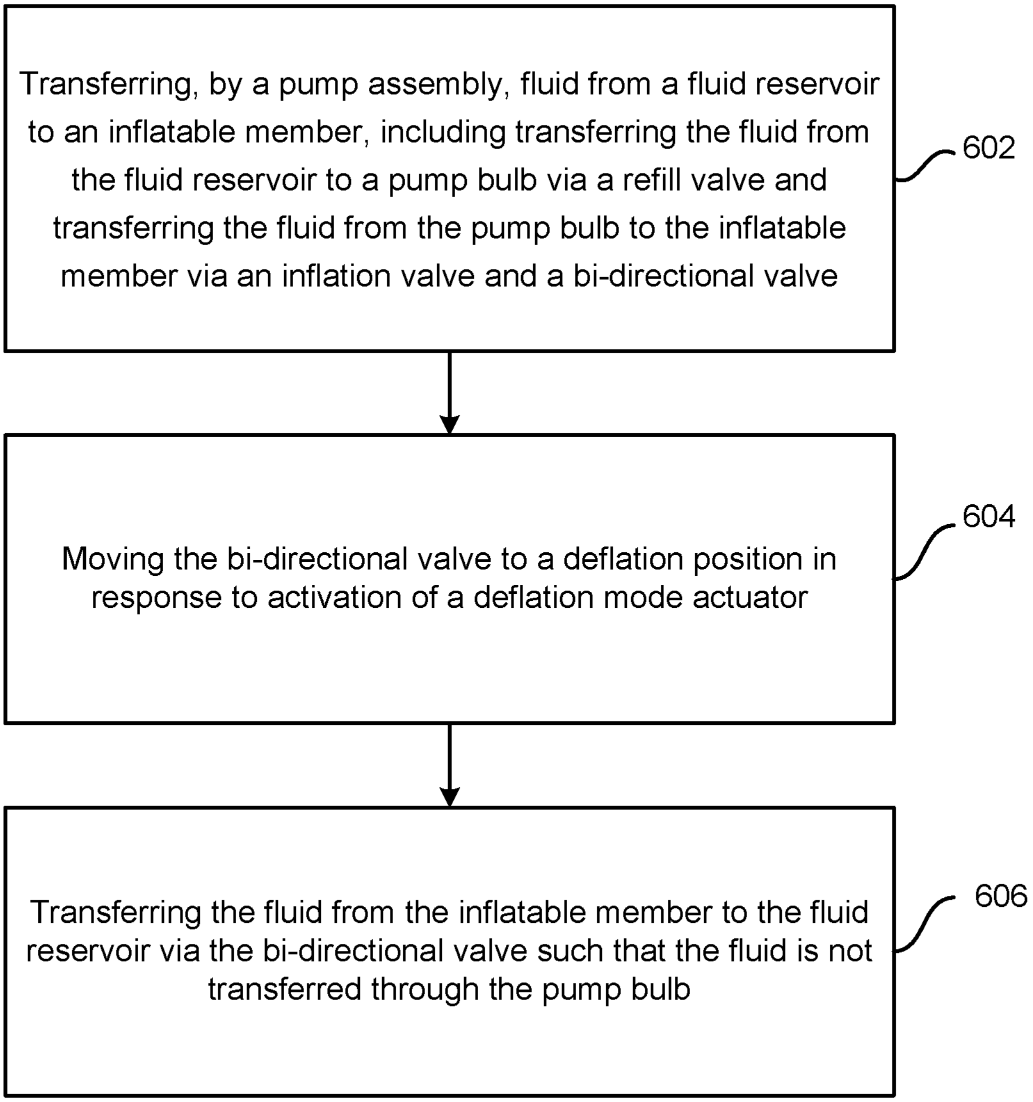
FIG. 6 illustrates a flow chart depicting example operations of a method of controlling a direction of fluid through a pump assembly of an inflatable penile prosthesis according to an aspect.

FIG. 6 illustrates a flow chart 600 depicting example operations of a method of controlling a direction of fluid through a pump assembly of an inflatable penile prosthesis according to an aspect. Although the flow chart 600 is explained with reference to the inflatable penile prosthesis 100 of FIG. 1, the example operations of the flow chart 600 may be performed by any of inflatable penile prostheses, pump assemblies, and/or bi-directional valves discussed herein.

Operation 602 includes transferring, by a pump assembly, fluid from a fluid reservoir to an inflatable member. For example, the pump assembly 106 may transfer fluid from the fluid reservoir 102 to the inflatable member 104. The transferring includes transferring the fluid from the fluid reservoir 102 to a pump bulb 108 via a refill valve 120, and transferring the fluid from the pump bulb 108 to the inflatable member 104 via an inflation valve 122 and a bi-directional valve 124.

Operation 604 includes moving the bi-directional valve to a deflation position in response to activation of a deflation mode actuator. For example, the bi-directional valve 124 may be moved to the deflation position in response to the activation of the deflation mode actuator 112.

Operation 606 includes transferring the fluid from the inflatable member to the fluid reservoir via the bi-directional valve such that the fluid is not transferred through the pump bulb. For example, the fluid is transferred from the inflatable member 104 to the fluid reservoir 102 via the bi-directional valve such that the fluid is not transferred through the pump bulb 108.

Figure 7:
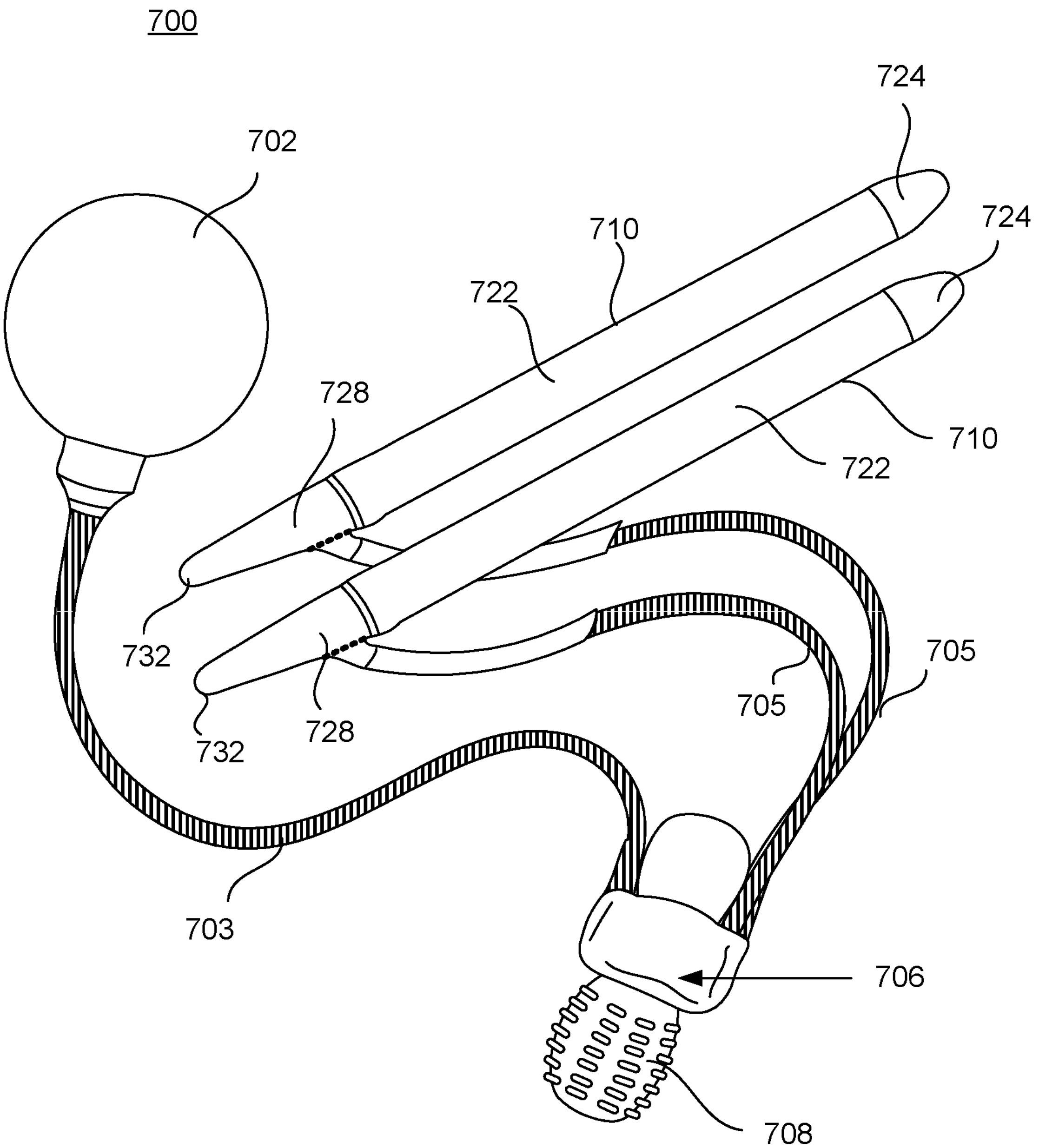
FIG. 7 schematically illustrates an inflatable penile prosthesis having a pump assembly according to an aspect.

FIG. 7 schematically illustrates an inflatable penile prosthesis 700 having a pump assembly 706 according to an aspect. The pump assembly 706 may include any of the features of the pump assemblies described with reference to the previous figures. The penile prosthesis 700 may include a pair of inflatable cylinders 710, and the inflatable cylinders 710 are configured to be implanted in a penis. For example, one of the inflatable cylinders 710 may be disposed on one side of the penis, and the other inflatable cylinder 710 may be disposed on the other side of the penis. Each inflatable cylinder 710 may include a first end portion 724, a cavity or inflation chamber 722, and a second end portion 728 having a rear tip 732.

The pump assembly 706 may be implanted into the patient's scrotum. A pair of conduit connectors 705 may attach the pump assembly 706 to the inflatable cylinders 710 such that the pump assembly 706 is in fluid communication with the inflatable cylinders 710. Also, the pump assembly 706 may be in fluid communication with a fluid reservoir 702 via a conduit connector 703. The fluid reservoir 702 may be implanted into the user's abdomen. The inflation chamber or portion 722 of the inflatable cylinder 710 may be disposed within the penis. The first end portion 724 of the inflatable cylinder 710 may be at least partially disposed within the crown portion of the penis. The second end portion 728 may be implanted into the patient's pubic region PR with the rear tip 732 proximate the pubic bone PB.

In order to implant the inflatable cylinders 710, the surgeon first prepares the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the inflatable cylinders 710. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 728. The surgeon may measure the length of the corpora cavernosae from the incision and the dilated region of the pubic area to determine an appropriate size of the inflatable cylinders 710 to implant.

After the patient is prepared, the penile prosthesis 700 is implanted into the patient. The tip of the first end portion 724 of each inflatable cylinder 710 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 710 into the corpus cavernosum. This is done for each inflatable cylinder 710 of the pair. Once the inflation chamber 722 is in place, the surgeon may remove the suture from the tip. The surgeon then inserts the second end portion 728. The surgeon inserts the rear end of the inflatable cylinder 710 into the incision and forces the second end portion 728 toward the pubic bone PB until each inflatable cylinder 710 is in place.

A pump bulb 708 of the pump assembly 706 may be squeezed or depressed by the user in order to facilitate the transfer of fluid from the fluid reservoir 702 to the inflatable cylinders 710. For example, in the inflation mode, while the user is operating the pump bulb 708, the pump bulb 708 may receive the fluid from the fluid reservoir 702, and then output the fluid to the inflatable cylinders 710. When the user switches to the deflation mode, at least some of the fluid can automatically be transferred back to the fluid reservoir 702 (due to the difference in pressure from the inflatable cylinders 710 to the fluid reservoir 702). Then, the user may squeeze the inflatable cylinders 710 to facilitate the further transfer of fluid through the pump bulb 708 to the fluid reservoir 702.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis comprising:
- a fluid reservoir configured to hold fluid;
- an inflatable member; and
- a pump assembly configured to transfer the fluid between the fluid reservoir and the inflatable member, the pump assembly including a valve body, a pump bulb, and a deflation mode actuator, the valve body including a bi-directional valve configured to move from an inflation position to a deflation position based upon an activation of the deflation mode actuator,
- the valve body including a first surface and a second surface opposite the first surface, the valve body includes a first deflation button extending from the first surface and a second deflation button extending from the second surface, the first deflation button being operatively coupled to the deflation mode actuator,
- the bi-directional valve in the inflation position configured to open a fluid passageway in the valve body to transfer fluid from the pump bulb to the inflatable member,
- the bi-directional valve in the deflation position configured to open a fluid passageway in the valve body to transfer fluid from the inflatable member to the fluid reservoir that bypasses the pump bulb.

2. The inflatable penile prosthesis of claim 1, wherein the bi-directional valve includes a control valve ball configured to move between the inflation position and the deflation position.

3. The inflatable penile prosthesis of claim 2, wherein the bi-directional valve includes at least one pusher member operatively coupled to the deflation mode actuator, the at least one pusher member configured to move the control valve ball to the deflation position.

4. The inflatable penile prosthesis of claim 3, wherein the at least one pusher member includes a first pusher member operatively coupled to the first deflation button, and a second pusher member operatively coupled to the second deflation button.

5. The inflatable penile prosthesis of claim 4, wherein actuation of either the first deflation button or the second deflation button moves the control valve ball to the deflation position.

6. The inflatable penile prosthesis of claim 1, wherein the deflation mode actuator includes a feedback component configured to provide at least one of tactile or auditory feedback to the activation of the deflation mode actuator.

7. The inflatable penile prosthesis of claim 1, wherein the pump assembly includes a plurality of fluid transfer ports that extend from the valve body, the plurality of fluid transfer ports including a reservoir fluid port, a first cylinder fluid port, and a second cylinder fluid port.

8. The inflatable penile prosthesis of claim 7, wherein the valve body includes a refill valve aligned with the reservoir fluid port, the refill valve configured to transfer fluid from the fluid reservoir to the pump bulb while the bi-directional valve is in the inflation position.

9. The inflatable penile prosthesis of claim 1, wherein the valve body includes an inflation valve fluidly coupled to the pump bulb.

10. The inflatable penile prosthesis of claim 1, wherein the valve body includes a refill valve, and an inflation valve, wherein the refill valve and the inflation valve are not used while the bi-directional valve is in the deflation position.

11. A pump assembly for an inflatable penile prosthesis comprising:
- a valve body including a bi-directional valve, the valve body including a first surface and a second surface opposite the first surface, the valve body includes a first deflation button extending from the first surface and a second deflation button extending from the second surface;
- a plurality of fluid transfer ports extending from the valve body, the plurality of fluid transfer ports including a reservoir fluid port and at least one cylinder fluid port;
- a pump bulb extending from the valve body; and
- a deflation mode actuator moveably coupled to the valve body and operatively coupled to the first deflation button,
- the bi-directional valve configured to move from an inflation position to a deflation position based upon an activation of the deflation mode actuator,
- the bi-directional valve in the inflation position configured to open a fluid passageway from the pump bulb to the at least one cylinder fluid port, the bi-directional valve in the deflation position configured to open a fluid passageway from the reservoir fluid port to the at least one cylinder fluid port that bypasses the pump bulb.

12. The pump assembly of claim 11, wherein the deflation mode actuator includes a feedback component configured to provide at least one of tactile or auditory feedback to the deflation button being pressed by a user.

13. The pump assembly of claim 11, wherein the valve body includes a refill valve disposed in a fluid passageway between the reservoir fluid port and the pump bulb, the refill valve being aligned along an axis that extends along a longitudinal axis of the reservoir fluid port, the refill valve configured to transfer fluid from the fluid reservoir to the pump bulb while the bi-directional valve is in the inflation position.

14. The pump assembly of claim 11, wherein the bi-directional valve includes a control valve ball and at least one pusher member operatively coupled to the deflation mode actuator, the at least one pusher member configured to move the control valve ball to the deflation position.

15. The pump assembly of claim 14, wherein the at least one pusher member includes a first pusher member operatively coupled to the first deflation button, and a second pusher member operatively coupled to the second deflation button.

16. The pump assembly of claim 11, wherein the valve body includes a refill valve, and an inflation valve, wherein the refill valve and the inflation valve are not used while the bi-directional valve is in the deflation position.

17. A method for controlling a direction of fluid through a pump assembly of an inflatable penile prosthesis, the method comprising:

transferring, by a pump assembly, fluid from a fluid reservoir to an inflatable member, a valve body including a first surface and a second surface opposite the first surface, the valve body includes a first deflation button extending from the first surface and a second deflation button extending from the second surface, including:

transferring the fluid from the fluid reservoir to a pump bulb via a refill valve;

transferring the fluid from the pump bulb to the inflatable member via an inflation valve and a bi-directional valve;

moving the bi-directional valve to a deflation position based on activation of a deflation mode actuator, the deflation mode actuator being operatively coupled to the first deflation button; and transferring the fluid from the inflatable member to the fluid reservoir via the bi-directional valve in a manner that the fluid is not transferred through the pump bulb.

18. The method of claim 17, wherein the refill valve and the inflation valve are not used to transfer the fluid from the inflation member to the fluid reservoir while the bi-directional valve is in the deflation position.

* * * * *